(12) United States Patent
Tsoukalis

(10) Patent No.: US 11,164,667 B2
(45) Date of Patent: Nov. 2, 2021

(54) METHOD FOR PROCESSING INFUSION DATA AND AN INFUSION PUMP SYSTEM

(71) Applicant: MICREL Medical Devices S.A., Gerakas (GR)

(72) Inventor: Achilleas Tsoukalis, Gerakas (GR)

(73) Assignee: MICREL Medical Devices S.A., Gerakas (GR)

( * ) Notice: Subject to any disclaimer, the term of this patent is extended or adjusted under 35 U.S.C. 154(b) by 0 days.

(21) Appl. No.: 14/791,989

(22) Filed: Jul. 6, 2015

(65) Prior Publication Data

US 2015/0306310 A1    Oct. 29, 2015

Related U.S. Application Data

(62) Division of application No. 14/182,111, filed on Feb. 17, 2014, now abandoned.

(30) Foreign Application Priority Data

Feb. 15, 2013  (GR) .................. 20130100089

(51) Int. Cl.
*A61M 5/142* (2006.01)
*G16H 20/17* (2018.01)
(Continued)

(52) U.S. Cl.
CPC ............ *G16H 20/17* (2018.01); *A61M 5/142* (2013.01); *A61M 5/16854* (2013.01);
(Continued)

(58) Field of Classification Search
CPC .......... A61M 5/16859; A61M 5/16854; A61M 2205/3561; A61M 5/142; A61M 2005/16868; A61M 2005/14208; A61M 2209/01; A61M 3/0216; A61M 2205/3553; A61M 2205/3584; A61M 2205/505;
(Continued)

(56) References Cited

U.S. PATENT DOCUMENTS 2,755,680 A    12/1956  Flubacker
4,530,696 A *   7/1985  Bisera ............... A61M 5/16859
                                                    128/DIG. 13
(Continued)

FOREIGN PATENT DOCUMENTS

EP         0431310       6/1991
WO      2009124134      10/2009
(Continued)

OTHER PUBLICATIONS

Search Report dated Jul. 17, 2014 from EP App. No. 14155405.5 7 pages.
(Continued)

*Primary Examiner* — William R Carpenter
(74) *Attorney, Agent, or Firm* — Bookoff McAndrews, PLLC

(57) ABSTRACT

A distributed infusion pump system is provided with long-term recording of the type of medication, nutrition or hydration, pump output pressure, corresponding infusion flow, infusion flow resistance, and an automatic or manual alarm in the event that thresholds applied to these parameters or their derivatives are exceeded.

27 Claims, 1 Drawing Sheet

(51) Int. Cl.
*A61M 5/168* (2006.01)
*G01L 19/12* (2006.01)
*G08B 21/18* (2006.01)

(52) U.S. Cl.
CPC ............ *G01L 19/12* (2013.01); *G08B 21/182* (2013.01); *A61M 2005/14208* (2013.01); *A61M 2005/16868* (2013.01); *A61M 2205/52* (2013.01)

(58) Field of Classification Search
CPC .... A61M 2005/16872; A61M 2205/14; A61M 2205/3576; A61M 2205/702; A61M 5/16831; A61M 2205/18; A61M 2205/70; G06F 19/3468; G06F 19/326; G06F 19/3412; G06F 19/3418; G06F 19/3443; G06F 19/3456
See application file for complete search history.

(56) References Cited

U.S. PATENT DOCUMENTS

| | | | | |
|---|---|---|---|---|
| 4,534,756 | A * | 8/1985 | Nelson | A61M 5/365 604/505 |
| 4,690,673 | A | 9/1987 | Bloomquist | |
| 4,836,752 | A | 6/1989 | Burkett | |
| 4,863,425 | A * | 9/1989 | Slate | A61M 5/16854 604/65 |
| 4,898,576 | A * | 2/1990 | Philip | A61M 5/16859 604/505 |
| 5,087,245 | A * | 2/1992 | Doan | A61M 5/16859 128/DIG. 12 |
| 5,096,385 | A | 3/1992 | Georgi et al. | |
| 5,116,203 | A * | 5/1992 | Natwick | A61M 5/14228 417/282 |
| 5,304,127 | A | 4/1994 | Kawahara et al. | |
| 5,356,378 | A | 10/1994 | Doan | |
| 5,445,622 | A | 8/1995 | Brown | |
| 5,609,576 | A | 3/1997 | Voss et al. | |
| 5,803,917 | A | 9/1998 | Butterfield et al. | |
| 5,814,015 | A | 9/1998 | Gargano et al. | |
| 5,827,223 | A * | 10/1998 | Butterfield | A61M 5/16859 604/65 |
| 5,935,099 | A | 8/1999 | Peterson et al. | |
| 6,158,965 | A | 12/2000 | Butterfield et al. | |
| 6,422,057 | B1 | 7/2002 | Anderson | |
| 6,551,243 | B2 * | 4/2003 | Bocionek | G16H 30/40 600/300 |
| 7,022,116 | B2 | 4/2006 | Morris | |
| 8,065,161 | B2 * | 11/2011 | Howard | A61M 5/142 604/131 |
| 8,551,038 | B2 | 10/2013 | Tsoukalis | |
| 2005/0055242 | A1 * | 3/2005 | Bello | G06F 19/3468 705/2 |
| 2005/0090799 | A1 | 4/2005 | Morris | |
| 2005/0096593 | A1 * | 5/2005 | Pope | A61M 5/1452 604/122 |
| 2009/0093774 | A1 * | 4/2009 | Wang | G01F 1/40 604/247 |
| 2011/0001605 | A1 * | 1/2011 | Kiani | G16H 40/00 340/5.6 |
| 2011/0295191 | A1 | 12/2011 | Injev | |
| 2012/0259282 | A1 | 10/2012 | Alderete, Jr. et al. | |
| 2015/0328396 | A1 * | 11/2015 | Adams | A61M 5/14216 604/500 |

FOREIGN PATENT DOCUMENTS

| | | |
|---|---|---|
| WO | WO2011080188 | 7/2011 |
| WO | WO2012024401 | 2/2012 |

OTHER PUBLICATIONS

Office Action dated Nov. 10, 2017 from EP App. No. 14155405.5, 5 pages.
Search Report from EP App. No. 18195297.9 dated Jan. 17, 2019.
Wong et al., "OPO36 Pump Infusion Pressures in Patients on Long Term Parenteral Nutrition: A Novel Approach and Monitoring Technique to Anticipate Catheter Occlusion", Oral Commucations & Controversies in Clinical Nutrition, vol. 36, Mar. 16, 2015.

* cited by examiner

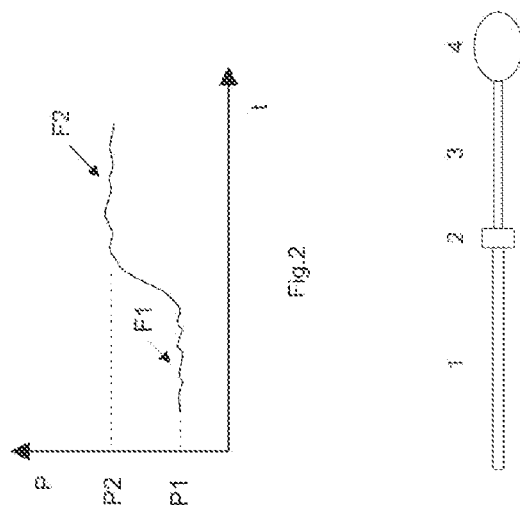
Fig.2
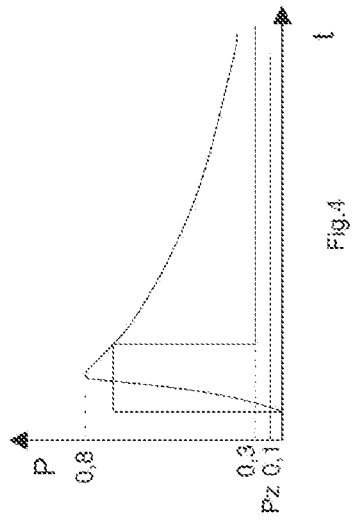
Fig.3
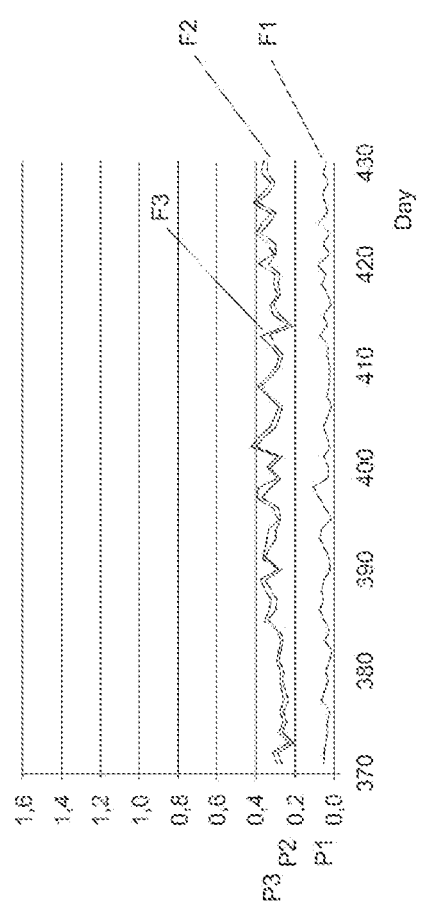
Fig.1
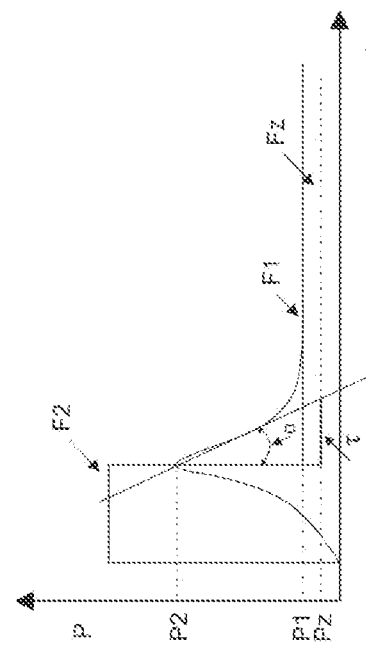
Fig.4
Fig.5

METHOD FOR PROCESSING INFUSION DATA AND AN INFUSION PUMP SYSTEM

CROSS REFERENCE TO RELATED CASES

This is a divisional of U.S. patent application Ser. No. 14/182,111, filed Feb. 17, 2014, which is hereby incorporated by reference in its entirety.

The present invention relates to a distributed infusion pump system.

Usually in infusion pumps, downstream pressure is monitored to reveal downstream occlusion. In the prior art, it is known to detect pressure levels of tissue type in subcutaneous infusions or leaks in the line or intravenous needle infiltration. In the present invention, we use infusion pressure statistics both steady state and transient, below occlusion level, for new medical practice and decisions per therapy.

In the case of long-term infusions into a central venous catheter, it is possible that the catheter will become blocked, requiring replacement, which would involve a new surgical intervention and additional discomfort for the patient. This occurs particularly in the case of parenteral nutrition, where the infusion lipids become gradually stratified and eventually block the catheter. A cleaning process is followed after each infusion, but the problem remains and is unpredictable at the current state of the art. Also vein obstructions have not been able to be predicted so far. In case of subcutaneous infusions such wherein the catheter is introduced erroneously into a nerve, which in most of such cases is not detected by x-rays, there is also no way to observe and recognize this error which is potentially harmful to the patient. Good catheter placement is also a problem in epidural and intrathecal infusions as well as in intravenous application where the needle is placed outside the vein (infiltration). In general, intravenous applications have a large fluid evacuation capability, resulting in a small increase of pressure with higher flow. In contrast thereto, in other types of application (subQ, epidural, intrathecal) the pressure of flow is built up pressure in a transient flow step up like a bolus, and reduced slower in a flow step down.

U.S. Pat. No. 8,551,038 discloses an infusion system in which the treatment results and side-effects of infusion are monitored remotely through a server as pumps are online exchanging data through or after therapy.

U.S. Pat. Nos. 5,609,576, 5,803,917, 5,087,245, 5,609, 576, 7,022,116, 2,755,680, 4,898,576, 5,087,245 and 6,158, 965 deal with the filtering or calculating of pressure downstream data in one or more flow levels due to a calculation of the line's flow resistance.

It is an object of the present invention to take into account pressure transience for medically useful conclusions and the provision of alarms.

In order to achieve the aforementioned and further objects, according to the present invention, there is provided a method for processing infusion data and an infusion pump system.

Further preferred embodiments and modifications of the present invention are defined in the dependent claims.

According to the present invention, processed are infusion pressure statistics considering both a steady state and a transient state, below occlusion level, for new medical practice and decisions per therapy. Pressure measurements in clinical trials on several infusion sites (not only intravenous) show that pressure/time graphs define an exponential type like a built-up infusion set occlusion pressure. So, according to the present invention, the pressure is monitored only at steady state and the decay from a given pressure with the pump stopped. This gives another great advantage that an infusion pump is not an ideal current source, as assumed in prior art models, so that the transient measuring when the pump is stopped for few seconds, gives accurate results. The present invention makes use of downstream pressure monitoring not only for short-term deductions concerning leaks but recording an event/pressure profile useful for extraction of useful medical decisions, like ones needed for regional analgesia nerve blocks, but also for long-term conclusions like obstruction of the central venous catheter, venous-SVC stenosis, and catheter blockage in the Parkinson's disease intestinal catheter.

The intention of the present invention is to provide an infusion pump system with downstream pressure recording means, to be used within both a short term (one infusion) and a long term over several infusions, for detection of defined problems, as for example infusion catheter blockage, SVC stenosis in chronic patients and regional analgesia nerve blockage complications, and for short term detection of medically useful information, like perineural infusion or generally pain treatment, over one single infusion lasting a few days.

Prediction of blockage before the venous catheter actually blocks has significant advantages for the patient, since even at an advanced stage of blockage, if even a small quantity of liquid is able to pass through the catheter, it can be cleaned, thus preventing a surgical intervention for replacement.

According to the present invention the type of fluid used in each infusion is recorded, a sampling time interval per therapy having single or multiple infusions duration is defined, and then an average downstream pressure during this interval including maximum pressure and maximum pressure difference is obtained. A pressure reading is always recorded at infusion rate transients even within an interval. Then, both rate and interval pressure statistics are recorded. Further, provided are means to display statistics graphs for one or more infusions, maybe over a day or many months, and for an algorithmic processing of said pressure/rate profiles for extracting medically useful information.

Said time interval is limited by data recording capacity of the system, it can be 10 seconds to one hour. A knowledge data base is maintained for each therapy, with fluid/rate/pressure/transient pressure normal data being stored and processed wherein abnormal data can issue a warning.

According to the present invention, used is a pressure threshold below occlusion, defined per therapy and per site type (subcutaneous, intravenous etc.) and possibly user. When said threshold is reached, special resistance of flow and time constants are measured and added to pressure statistics stored in the data base of the pump or the server (distributed pump system). When pressure statistic limits as defined by user are exceeded, an alarm or warning according to the therapy and risks identified is issued. According to the present invention, the knowledge is built over a long term, through experience by considering false alarms vs. correct alarms. The risk of percentage of false alarms is taken by user, who defines the amount of false alarms he can accept, just to prevent a higher risk of real alarms that need possibly surgical intervention. So warning and/or alarm limits or warning communication (to whom/when) are also defined by a user group or the user and the therapy. For example, in a clinical study on parenteral nutrition pressure monitoring over hundreds of patients and almost a year of monitoring, only 2 patients showed pressure peaks being higher than 0.5 bar wherein one of them needed a medical intervention (venoplasty) and in the other case there was a false alarm.

However, the risk of false alarms defining 0.5 bar as pressure limit for a catheter vein problem warning is definitively small (1 false over hundreds no-alarm). For building up a system knowledge, doctors report false and real alarms to the system stored in the data base per therapy and also user group. So, when a user or doctor selects some alarm and/or warning parameters for a therapy and patient type (fat/slim, race etc.), the system will warn him about the percentage of error these parameters can expect.

Preferably, this is possible by a telemedicine system described in U.S. Pat. No. 8,551,038 in combination with the present invention, wherein a parametric definition of alarm and/or warning, communication type and urgency (text on mobile, email, alarm on pump), pressure level statistics, resistance of flow, transient time constant and sampling time are defined per therapy, gained experience and user risk acceptance so they are not fixed as in the prior art. Provided are means to users to define the parameters and possibly some already known propositions gained from ongoing clinical trials in parenteral nutrition and peripheral nerve blockage. This information may help clinicians modify early the infusion parameters of regional analgesia that depend a lot from how much distant is the catheter from the nerve.

After all, an aspect of the present invention is the recording of pressure data below occlusion level and creating a graph of said data for deduction of medically useful information. A further aspect of the present invention is the definition of a time interval per therapy for pressure data recording which time interval reduces the data to be sent.

A further aspect of the present invention is the measurement of the pressure data not only from one pump as in the prior art, but for many pumps and in many times so as to build up a group knowledge like an ongoing clinical trial.

Preferably, downstream pressure statistics data are grouped in accordance with a) therapy, b) drug, c) way of introduction (intravenous, epidural, perineural, subcutaneous etc.), d) type of delivery (needle, central venous catheter, small perineural catheter, angled needle etc.), e) reported problem type, f) alarm and/or warning level, and g) user type so as to show results according to choices from some or all the aforementioned groups a to g. So, it can be asked e.g. for all reported catheter "type z", "obstructions" and "statistics" during the "last month of use for each catheter", so that a query is transferred to the database. Problems are preferably reported to the system by caregivers with reference to category (obstruction of catheter, obstruction of a vein, semi-obstruction etc) and part used (e.g. catheter brand or a model) so as to build up a knowledge on which group of data a problem arises. A risk factor of statistical data and/or reported problems is evaluated by the user or by an automatic computerized process (e.g. comprising neural networks or other artificial intelligence or data filtering and/or algorithmic processing). Preferably, alarm and warning limits are chosen per user after his risk analysis or acceptance, and then applied to the system, i.e. in particular an alarm appropriate for the user so that he/she does not need to be bothered by many or too many of the "medical type" alarms, and/or a warning for infiltration on P-average<x, and τ<y or intraneural alarm if Pmax>x and τ>y or the need of the catheter to be cleaned if A>x and τ>y etc., wherein this process is not static as in the prior art, but changing as knowledge is building up.

According to a further aspect of the present invention, there is provided a distributed infusion pump system comprising means for measuring and calculating downstream pressure statistics per infusion and per rate, a database to store said statistics linked per infusion attributes (date, patient type, name, delivery route, catheter type, needle type, drug, therapy), means to report and link specific infusion's attributes into said database a health thread or event (catheter block, infiltration, intraneural placement), means to query all database comprising thousands of patients and infusions over long time period according to attributes and events and statistics, so as to decide on infusion pump limits for warning/alarm per heath thread or event type, and means to transfer these alarm/warning limits to the pump system as alarm/warning per type.

In the following, preferred embodiments of the present invention will be described with reference to the accompanying drawings, wherein FIG. 1 is a graph showing a typical long term pressure recording in parenteral nutrition for various fluids, FIG. 2 is a graph showing a transition from a first flow and pressure to a second flow and pressure, FIG. 3 shows a typical infusion drug delivery chain, FIG. 4 is a graph showing a loading dose and intraneural pressure long drop, and FIG. 5 is a graph showing a standard subcutaneous loading dose pressure transient.

FIG. 3 schematically shows a typical drug delivery chain comprising an infusion set 1, a connector 2, a catheter 3 and a tissue or vein 4 wherein the connector 2 couples the infusion set 1 with the catheter 3 which is introduced into the tissue or vein 4.

In parenteral nutrition, there are different types of infusion, i.e. for main nutrition and for hydration or combination of both (dilutions). For nutrition the average flow speed for adults is 120 ml/hr, and for hydration it is the maximum pump flow, e.g. 400 ml/hr. Typical parenteral nutrition pressure graphs are shown in FIG. 1. For a long term recording, the pump initially records statistical information about downstream pressure of the infusion such as average pressure, maximum pressure and maximum pressure difference, together with how many peaks happened, and duration per peak, for the entire infusion. When connected to a so-called distributed system as described in U.S. Pat. No. 8,551,038, pressure interval (one hour), statistics and flow profile data are uploaded to a telemedicine server. Pressure statistics include a calculated flow resistance A and a transient time constant T. Average can be a real average or the result of digital filtering on the pressure data. Pump system (pump screen or web server) can display graphs of statistical curves, or warn the user if abnormal peaks or trends are found.

The system makes time-stamped recordings of the pressure statistics and/or rates, so that a physician or an automated decision-making system evaluates the increase of pressure below occlusion and consequently informs the patient, who can also monitor the pressure statistic curves on the pump. Thanks to local and remote long term recording and the display of pressure statistics, surgical intervention can be avoided. A clinical trial in a hospital has shown that the recording of the statistics on output pressure for each infusion rate in each patient demonstrates the catheter's tendency to block (several months recording).

In intravenous infusions such as a parenteral nutrition, pressure is usually between 0.1 and 0.5 bar. Pressure difference peaks of more than 0.5 bar and, hence, below occlusion level have showed Superior Vena Cava stenosis needing venoplasty.

Resistance of flow in an open end tube is A=P/F where P is a steady state pressure for a flow (infusion rate) F, wherein a general tendency for block, i.e. an increase of resistance of flow such as an increase of pressure at a constant flow, can be observed. In the parenteral nutrition example above, said pressure statistics comprise such resistance of flow.

In the prior art, resistance of flow at steady state of intravenous infusions is calculated by the formula $$A = \frac{P2 - P1}{F2 - F1}.$$

FIG. 2 shows a transition from flow F1 and pressure P1 to flow F2 and pressure P2.

In another embodiment of the present invention, pressures and corresponding flows recorded in nutrition and hydration (or under different speeds for the same liquid) are used to calculate the resistance of flow giving indications on the catheter condition. So, the resistance of flow A is calculated from different pressure and flow which occur with the different infusions and/or even on different days, and this is new in the art. With respect thereto, it is referred to FIG. 1 which as an example shows graphs representing three different flows F1, F2 and F3 under different pressure P1, P2 and P3, respectively. Due to the differing viscosity of different fluids, the flow resistance calculated is not the real figure, but its trend over time reveals whether or not there is a verge of blockage and the catheter needs cleaning. To compensate this, normalized formula for resistance of flow is calculated as $$A = \frac{(P2 - P1) * Vw}{((F2 - F1) * Vs)}$$

where viscosity of water Vw and viscosity of drug Vs have been added which for drugs with high viscosity as immunoglobulin is important.

In another embodiment of the present invention, the pump can run a slow flow plus a fast flow and calculate the flow resistance, at the beginning or the end of the infusion wherein the end seems best because sugar intake has been completed and the adult patient is not at risk, i.e. flow resistance calculated within one single infusion.

The local display at the pump or the remote, mobile or internet application, displays the pressure statistics and corresponding flow and also potentially the flow resistance in a diagram chronologically where the trend appears. The derivative of the pressure curve over time, i.e. the pressure's tendency to increase over time (days, weeks, months or years), is also displayed, for easy computation by an automated system, the patient or the physician, so as to create a figure or drawing of conclusions regarding the potential blockage of the catheter in the near future. The derivative during and after a bolus (high rate specific volume infusion) gives useful information especially at subcutaneous infusions, where cavities (very slow change) or dead space and/or high change (inside a nerve) can be detected.

The system according to the present invention can also be used in cases other than central venous catheters, e.g. for Duodopa infusions in patients with Parkinson's disease, to prevent the blockage of duodenal stomach or peritoneal catheters, in infusions for peripheral analgesia where the involuntary relocation of the catheter near the nerve shows a sudden change in the output pressure, translated into alterations in the analgesia, so that changes to the anaesthetic dosage are required.

The resistance of flow is independent of flow. Bolus time may not be generally enough to reach a pressure steady state for the flow rate, so that a measurement of transient fall times is taken for calculating a time constant τ.

The flow resistance is not only measured in subcutaneous, epidural and intrathecal infusions, as pressure is built up relatively fast after a flow step, whereas a decay is relatively slow. So, according to the present invention, a transient response to flow and/or pressure only in the pressure decay after a high rate down to zero rate is measured.

Some measured curves in the data have an almost linear slope and some are exponential as shown as an example in FIGS. 4 and 5. So, the time constant in the decay from step to zero rate is measured wherein the found curve is always of the same type. This eliminates another type of error, i.e. the assumption of an ideal flow source in the prior art model, as the flow rate is not ideal, resulting in the introduction of errors. Zero rate is selected so that no forced flow intervenes in the flow decay, also because the steady state pressure of the asymptote Pz is known. This can be the medium pressure measured when after purge the pump is connected to the patient, just before the infusion starts, or measured close to a low infusion rate before a high flow step (bolus/loading dose). So, the transient time constant and resistance of flow are calculated easily and relatively fast.

This measurement is also used in intravenous infusions, stopping for some seconds a relatively high rate (above 100 ml/hr) usual as in intravenous infusions.

In subcutaneous infusions, such as regional analgesia, with a catheter placed in surgery, the recording time interval can be 30 seconds, and the transient pressure after a maximum rate bolus is recorded followed by recording the decay of pressure at a generally low following basal rate, to show if the catheter is placed into a nerve which is potentially harmful to the patient. The pressure rise and fall times are different depending on the placement of a peripheral nerve blocking catheter in surgery. This can give information regarding a reposition of the catheter and the avoidance of complications or a prediction for a based infusion and bolus needed, when the patient goes home. FIG. 5 shows a normal transient response during and after a loading dose and bolus; and FIG. 4 shows an intraneural transient response i.e. with limited space and elasticity so that the pressure rises abruptly and decays slowly.

The decay initial linear portion of the exponential gives points (P,t) defining through linear regression (least squares) a slope angle α (FIG. 5) which in theory (initial slope method) intersects the steady state pressure Pz at time point τ. From that triangle τ calculated by the formula τ=(P-Pz)*sin(a) where P is the starting pressure before decay, when zero infusion rate starts, and Pz is the zero rate pressure known as above. This measurement can last a few seconds. Alternatively for fast decaying curves, point (τ, 37% (P-Px)) defines τ with the pressure Pt=37% of (P-Pz) when the time point t=τ is constant.

As described above, according to the present invention, means are provided for recording a downstream pressure statistics of an infusion at specific time intervals, with mean, maximum and minimum (or maximum difference) pressure within the interval, wherein the intervals depend on the therapy type, and a calculation of statistical methods so to extract useful medical information, such as resistance of flow A=P/F at steady state, and formula A when pressure and flow differences and a transient time constant T have been obtained, and where said recording can be provided for more than one infusions on the same patient and same catheter, means for displaying such raw and calculated statistics (in contrast to also uploaded and recorded feedback from reported problems) so that medically useful information can easily be deducted from an automated system or the doctor wherein this information gives parameters for the user to define limits per therapy, and wherein a knowledge base is structured by user feedbacks on limits used and false or correct alarms given by the system so that continuous improvement of results can be achieved through telemedicine.

The invention claimed is:

1. A method for processing infusion data for a distributed infusion pump system, the distributed infusion pump system comprising at least an infusion pump and a computer system operatively coupled to the infusion pump, the method comprising:
measuring, using the infusion pump, a downstream pressure during an infusion;
providing downstream data related to the measured downstream pressure from the infusion pump to the computer system;
in the computer system, (a) storing in a non-transitory database the downstream data provided from the infusion pump, (b) linking the stored downstream data with infusion attributes, and (c) linking the infusion attributes with a health event type caused by a condition selected from at least one of a catheter block, an infiltration, or an intraneural placement, the database including patient data from a plurality of patients and infusion data from a plurality of infusions over a time period;
determining, using the computer system, one or more infusion pump limits for each of a plurality of health event types for each of the conditions, wherein each of the infusion pump limits is associated with a corresponding health event type and the infusion is associated with a corresponding health event, the one or more infusion pump limits being based on the infusion attributes, the patient data from the plurality of patients, and the infusion data from the plurality of infusions over a time period, wherein an infusion pump limit is temporally reached prior to an occurrence of its corresponding health event type;
storing, at the database in the computer system, at least one infusion pump limit profile for each of the plurality of health event types for each of the conditions;
selecting, from the database in the computer system, one or more selected infusion pump limits for warning and/or alarm for the health event type corresponding to the infusion based at least on the at least one infusion pump limit profile for the health event type, wherein the health event type corresponding to the infusion includes a parenteral nutrition or a peripheral nerve blockage, and wherein the one or more infusion pump limits are related to an acceptable percentage of false alarms; and
setting the selected one or more infusion pump limits in the infusion pump as an alarm and/or warning for the health event type corresponding to the infusion.

2. The method according to claim 1, wherein the downstream data provided from the infusion pump to the computer system comprise a resistance of flow (A) and a time constant ($\tau$).

3. The method according to claim 2, wherein the time constant ($\tau$) is determined after the resistance of flow (A) reaches a predetermined limit, or the pressure reaches a predetermined downstream occlusion level, where the infusion stops (rate=0) for the measurement and continues or waits for alarm release.

4. The method according to claim 2, wherein the time constant ($\tau$) is determined after a bolus end, and the infusion is stopped until the time constant ($\tau$) is determined.

5. The method according to claim 2, wherein the resistance of flow (A) is determined from different infusions with different rates and drugs on the same patient.

6. The method according to claim 5, wherein the resistance of flow (A) is determined from different infusions with different rates, drugs, and attributes on the same patient.

7. The method according to claim 1, further including, measuring, using the infusion pump, a zero rate downstream pressure before starting an infusion.

8. The method according to claim 1, wherein the infusion attributes comprise at least one of date, patient type, name, delivery route, catheter type, needle type, drug, or therapy.

9. The method according to claim 1, wherein alarms and/or warnings are conveyed to a user by at least one of showing a message on a web page, by mobile phone text messages, email, or alarm on a pump.

10. The method according to claim 1, wherein the downstream data related to the measured downstream pressure comprise one or more of maximum pressure, average pressure, or maximum pressure difference.

11. The method according to claim 1, wherein measuring the downstream pressure includes stopping infusion while downstream pressure measurement is performed.

12. The method according to claim 1, further including, measuring using the infusion pump, infusion rate.

13. The method according to claim 1, further including, comparing the downstream data related to the measured downstream pressure with a threshold value (T) which indicates a risk of blockage of the infusion pump, wherein the threshold value (T) is lower than a value that indicates actual blockage.

14. The method according to claim 13, wherein the threshold value (T) is dependent upon the type of the infusion fluid, the way of introduction of the infusion fluid and/or type of delivery means.

15. The method according to claim 13, wherein the threshold value (T) is recalculated based on the measured downstream pressure and/or risk of blockage indicated by the system.

16. The method according to claim 1, wherein the computer system is remotely located from the infusion pump.

17. The method according to claim 16, wherein downstream data from more than one infusion pump are received by the remote computer system.

18. The method according to claim 1 wherein an alarm is given if a pressure value greater than or equal to a threshold value (T) is measured.

19. The method according to claim 1, wherein the downstream data related to the measured downstream pressure include minimum pressure, maximum pressure, and/or average pressure, and/or maximum difference of pressure during a sampling period.

20. The method according to claim 1, wherein a first infusion pump limit for a first health event type from the plurality of health event types is different than a second infusion pump limit for a second health event type from the plurality of health event types.

21. The method according to claim 1, further comprising:
determining the one or more infusion pump limits for each of the plurality of health event types further based on site types, wherein each health even type is associated with at least one site type and at least one type of delivery, wherein the at least one infusion pump limit profile for each of the plurality of health event types comprises a corresponding site type;

receiving an infusion site type for the infusion at the computer system;

selecting the one or more selected infusion pump limits for the health even type further based on the infusion pump limit profile comprising the infusion site type.

22. A method for processing infusion data, comprising:
measuring pressure downstream of one or more infusion pumps;
calculating, using the one or more infusion pumps, downstream pressure statistics per infusion and per rate;
storing in a non-transitory database of a computer system associated with the one or more infusion pumps, the calculated statistics linked per infusion attributes, wherein the database includes infusion data related to multiple patients and multiple infusions over a time period;
linking, in the database, an infusion attribute with a health event type caused by a condition selected from at least-one of a catheter block, an infiltration, or an intraneural placement; health event type caused by a condition selected from at least
determining, using the computer system, one or more infusion pump limits for each of a plurality of health event types for each of the conditions, wherein each of the infusion pump limits is associated with a corresponding health event type and the infusion is associated with a corresponding health event, the one or more infusion pump limits being based on the infusion attributes, the patient data from the plurality of patients, and the infusion data from the plurality of infusions over a time period, wherein an infusion pump limit is temporally reached prior to an occurrence of its corresponding health event type;
storing, at the database in the computer system, at least one infusion pump limit profile for each of the plurality of health event types for each of the conditions;
selecting, from the database, selected infusion pump limits for warning or alarm for the health event type corresponding to the infusion based at least on the at least one infusion pump limit profile for the health event type, wherein the health event type corresponding to the infusion includes a parenteral nutrition or a peripheral nerve blockage, wherein the infusion pump limits are related to an acceptable percentage of false alarms; and
transferring the selected infusion pump limits from the computer system to the one or more infusion pumps; and
setting the transferred infusion pump limits as alarm or warning limits in the one or more infusion pumps for the health event type corresponding to the infusion.

23. The method according to claim 22, wherein the infusion attributes comprise at least one of date, patient type, name, delivery route, catheter type, needle type, drug, or therapy.

24. A method for processing infusion data, comprising:
(a) measuring, using an infusion pump, a downstream pressure during an infusion;
(b) comparing, using the infusion pump, the measured downstream pressure with a threshold value (T) which indicates a risk of blockage of the infusion pump, wherein the threshold value (T) is lower than a value that indicates actual blockage;
(c) providing downstream data related to the measured downstream pressure from the infusion pump to a computer system operatively coupled to the infusion pump, wherein the downstream data comprise a resistance of flow (A) and a time constant ($\tau$);
(d) in the computer system, (i) storing in a non-transitory database the data received from the infusion pump, (ii) linking the stored downstream data with infusion attributes, and (iii) linking the infusion attributes with a health event type caused by a condition selected from at least one of a catheter block, an infiltration, or an intraneural placement, such that the database includes a plurality of patient data and infusion data for a plurality of infusions over a time period, wherein, when the measured downstream pressure equals the threshold value (T) in step (b), a special resistance of flow and a special time constant ($\tau$) are determined and added to the database;
(e) determining, using the computer system, one or more infusion pump limits for each of a plurality of health event types for each of the conditions, wherein each of the infusion pump limits is associated with a corresponding health event type and the infusion is associated with a corresponding health event, the one or more infusion pump limits being based on the infusion attributes, the patient data from the plurality of patients, and the infusion data from the plurality of infusions over a time period, wherein an infusion pump limit is temporally reached prior to an occurrence of its corresponding health event type;
(f) storing, at the database in the computer system, at least one an infusion pump limit profile for each of the plurality of health event types;
(g) selecting, from the database in the computer system, one or more selected infusion pump limits for warning and/or alarm per health event type corresponding to the infusion based at least on the at least one infusion pump limit profile for the health event type, wherein a health event type corresponding to the infusion includes a parenteral nutrition and a peripheral nerve blockage, wherein the one or more infusion pump limits are related to an acceptable percentage of false alarms; and
(h) setting the selected one or more infusion pump limits in the infusion pump system as an alarm and/or warning for the health event type corresponding to the infusion.

25. The method according to claim 24, wherein providing the downstream data related to the measured downstream pressure from the infusion pump to a computer system includes uploading data from the infusion pump to the computer system that is remotely located from the infusion pump.

26. The method according to claim 24, wherein, when the measured downstream pressure equals the threshold value (T) in step (b), a notification is issued via at least one of a message on a web page, a text message, or an alarm on a pump.

27. The method according to claim 24, wherein the infusion attributes comprise at least one of date, patient type, name, delivery route, catheter type, needle type, drug, or therapy.

* * * * *